United States Patent [19]

Seitzer

[11] 4,086,289

[45] Apr. 25, 1978

[54] MANUFACTURE OF XYLENES

[75] Inventor: Walter H. Seitzer, West Chester, Pa.

[73] Assignee: Sun Oil Company of Pennsylvania, Philadelphia, Pa.

[21] Appl. No.: 813,158

[22] Filed: Jul. 5, 1977

[51] Int. Cl.² ............................................. C07C 3/52
[52] U.S. Cl. ........................... 260/671 M; 252/455 Z;
260/671 R; 260/671 C
[58] Field of Search .......... 260/671 R, 671 M, 671 C;
252/455 Z

[56] References Cited

U.S. PATENT DOCUMENTS

| | | | |
|---|---|---|---|
| 3,121,754 | 2/1964 | Mattox et al. | 260/671 R |
| 3,187,063 | 6/1965 | Burk et al. | 260/671 M |
| 3,718,704 | 2/1973 | Chapman et al. | 260/671 M |

Primary Examiner—Delbert E. Gantz
Assistant Examiner—C. E. Spresser
Attorney, Agent, or Firm—J. Edward Hess; Donald R. Johnson; Paul Lipsitz

[57] ABSTRACT

In the process of methylating toluene to obtain a mixture of xylenes by contacting toluene with hydrogen and a carbon oxide-containing gas in the presence of a catalyst, the improvement of using as catalyst zinc chromite mixed with an alkali metal exchanged molecular sieve containing a stoichiometric excess of an alkali metal carbonate, whereby a more favorable proportion of p-xylene is obtained.

3 Claims, No Drawings

MANUFACTURE OF XYLENES

This invention relates to the methylation of toluene to obtain a mixture of xylene isomers and produces an isomer mixture which has a low proportion of the undesirable m-isomer. A further advantage of the process is that it is low in unwanted ethyl benzene by-product. The mixture obtained by the process of the invention lends itself to easy separation of the highly desired p-xylene and obviates the difficulties encountered with the usual equilibrium mixture of xylenes (o:m:p = 1:1:2.3) where the high proportion of the meta isomer interferes with separation of the desired ortho and para isomers. Such mixtures of the prior art also contain up to 10% ethylbenzene. In current practice the ortho isomer is first distilled off. The para isomer is recovered by crystallization. Complete recovery of the p-xylene is limited by the eutectic formed with meta xylene as well as by the presence of ethyl benzene. Thus, a method of obtaining p-xylene more efficiently would provide an important advance in the art.

It is known in the art to effect methylation of aromatic hydrocarbons by reaction with a carbon oxide in the presence of catalysts such as copper oxide-chromia, zinc oxide-copper oxide, and zinc chromite. Such a process is disclosed in U.S. Pat. No. 3,718,704, but when using such a process with toluene as the aromatic compound, the isomer distribution is unfavorable to the para isomer.

It has now been found that this methylation reaction can be modified so as to give as product a mixture of xylenes which is relatively low in the proportion of meta-xylene and very low in ethyl benzene content. This is achieved by using as catalyst for the reaction of toluene with hydrogen and a carbon oxide a zinc chromite catalyst mixed with an alkali metal treated exchanged molecular sieve.

The general procedure for the reaction is fully described in the above mentioned U.S. Pat. No. 3,718,704 which disclosure is hereby incorporated by reference. In general, the process involves feeding toluene to a reactor where it is contacted with a mixture of hydrogen and a carbon oxide containing gas in the presence of the catalyst at a temperature between 250° C, and about 650° C, at a liquid hourly space velocity (LHSV, volume of liquid feed/hour/volume of catalyst) of about 0.17 to about 17, a gaseous hourly space velocity of from about 100 to about 5000, and a pressure of zero to 15,000 psig.

The carbon-oxide containing reactant gas will contain carbon monoxide and/or carbon dioxide. The carbon oxide containing reactant gas may also contain the hydrogen rather than introducing the hydrogen gas separately. The preferred carbon-oxide is carbon monoxide. The gaseous reactants may also contain other gases which are considered inert (i.e., gases which would not adversely affect the reaction and/or the product).

The ratio of hydrogen to carbon-oxide in the gas is from about 0.5 to 1 to about 10 to 1. For some reactants in commercial scale facilities, large volumes of hydrogen may be helpful as a heat sink to help control reaction temperature and prevent formation of undesirable by-products from side reactions. The preferred ratio of hydrogen to carbon-oxide is between about 1 to 1 and about 6 to 1, with the most preferred ratio being about 2 to 1.

The zinc chromite catalyst is commercially available, an example of which is Zn-0308T available from Harshaw which contains 22% $Cr_2O_3$ and 78% ZnO, with a surface area of between 110 and 130 $m^2/gm$. Other useful catalysts are Harshaw's Zn-0311 and Zn-0312.

The cocatalyst as indicated will be an alkali metal treated molecular sieve. Such materials are well known and include the alkali metal forms of natural and synthetic zeolites. To obtain the cocatalyst for use in this process the molecular sieve is simply treated with the desired alkali metal salt, as is known in the art, to obtain the exchanged material. The alkali metal salt will be used in excess of that required for stoichiometric exchange and such excess of alkali metal will preferably be from about 1 to about 5% by weight of the sieve, although it could be as high as about 10%. Alternatively, excess alkali metal salt may be added to a stoichiometrically exchanged molecular sieve. Suitable alkali metal salts will include the sodium, potassium, and other alkali metal carbonates, bicarbonates, hydroxides and the like. The preferred zeolite is a potassium exchanged 13X molecular sieve.

The following table illustrates the process of this invention in giving the desired low proportion of meta-isomer containing product which is also free of ethyl benzene.

TABLE I

METHYLATION OF TOLUENE
450° C, 750 psig, CO:$H_2$ = 1.1, GHSV = 1200, LHSV = 0.3

| Pressure (Psig) | Catalyst | $C_8$ Yield(%) | Xylene Isomer Ratio (o:p:m) | % Ethyl benzene |
|---|---|---|---|---|
| 750 | Zn 0312 | 10.4 | 1:1.8:3.2 | 2.9 |
| 750 | Zn 0311 + KX* | 9.9 | 1:1.6:2.8 | 3.0 |
| 750 | Zn 0311 + K-13X** | 11.3 | 1:0.63:0.67 | 0.0 |

*Equal amounts of Zn 0311 (zinc chromite) and stoichiometrically potassium exchanged 13X Linde molecular sieve.
**Equal amounts of Zn 0311 (zinc chromite) and 13X Linde molecular sieve which contained 2% potassium carbonate in stoichiometric excess.

As calculated from the above table, the ratio of meta-isomer to para-isomer is about 1.8 for the two runs without the cocatalyst, whereas with the cocatalyst that ratio is about 1.1. In general the process of the invention will produce a product where the m:p ratio is less than 1.5 and frequently less than 1.0.

The invention claimed is:

1. In the process of methylating toluene to obtain a mixture of xylenes relatively low in the meta-isomer and low in ethyl benzene content by contacting toluene with hydrogen and a carbon oxide-containing gas in the presence of a catalyst, the improvement of using as catalyst zinc chromite mixed with an alkali metal exchanged molecular sieve containing a stoichiometric excess of an alkali metal carbonate.

2. The process of claim 1 where the molecular sieve is a zeolite.

3. The process of claim 2 where the alkali metal is potassium.

* * * * *